United States Patent
Gu

(10) Patent No.: US 11,157,081 B1
(45) Date of Patent: Oct. 26, 2021

(54) APPARATUS AND METHOD FOR USER INTERFACING IN DISPLAY GLASSES

(71) Applicant: Shenzhen Yunyinggu Technology Co., Ltd., Shenzhen (CN)

(72) Inventor: Jing Gu, Shenzhen (CN)

(73) Assignee: SHENZHEN YUNYINGGU TECHNOLOGY CO., LTD., Shenzhen (CN)

(*) Notice: Subject to any disclaimer, the term of this patent is extended or adjusted under 35 U.S.C. 154(b) by 0 days.

(21) Appl. No.: 16/941,119

(22) Filed: Jul. 28, 2020

(51) Int. Cl.
| | |
|---|---|
| *G06F 3/01* | (2006.01) |
| *A61B 5/291* | (2021.01) |
| *A61B 5/296* | (2021.01) |
| *G02B 27/01* | (2006.01) |
| *A61B 5/00* | (2006.01) |

(52) U.S. Cl.
CPC .............. *G06F 3/015* (2013.01); *A61B 5/291* (2021.01); *A61B 5/296* (2021.01); *A61B 5/4542* (2013.01); *A61B 5/7264* (2013.01); *G02B 27/0101* (2013.01); *G02B 27/0172* (2013.01); *G02B 27/0176* (2013.01); *G06F 3/013* (2013.01); *G02B 2027/0138* (2013.01); *G02B 2027/0178* (2013.01)

(58) Field of Classification Search
CPC ......... G06F 3/015; A61B 5/291; A61B 5/296; G02B 27/0172; G02B 27/0101
USPC ....................................... 345/156
See application file for complete search history.

(56) References Cited

U.S. PATENT DOCUMENTS

| | | | | |
|---|---|---|---|---|
| 5,930,741 | A * | 7/1999 | Kramer | G06F 3/011 702/153 |
| 6,636,763 | B1 * | 10/2003 | Junker | G06F 3/013 340/4.11 |
| 9,819,782 | B1 * | 11/2017 | Daniels | H04M 1/05 |
| 2006/0028400 | A1 * | 2/2006 | Lapstun | H04N 13/344 345/8 |
| 2007/0083097 | A1 * | 4/2007 | Fujiwara | A61B 5/14553 600/407 |
| 2009/0264788 | A1 * | 10/2009 | Shyu | A61B 5/378 600/544 |
| 2012/0069247 | A1 * | 3/2012 | Morikawa | G06F 3/015 348/734 |
| 2012/0245713 | A1 * | 9/2012 | Chen | G06F 3/015 700/83 |
| 2014/0347265 | A1 * | 11/2014 | Aimone | G02C 11/10 345/156 |
| 2015/0277560 | A1 * | 10/2015 | Beaty | G06F 3/015 345/156 |

(Continued)

FOREIGN PATENT DOCUMENTS

EP     3396495 A1 * 10/2018 ............. G06F 3/015

*Primary Examiner* — Chineyere D Wills-Burns
(74) *Attorney, Agent, or Firm* — Bayes PLLC

(57) ABSTRACT

A wearable apparatus for display glasses, according to certain embodiments, can include a display that includes a pair of screens configured to be mounted in front of respective eyes of a face of a wearer of the apparatus. The display can be configured to provide a display of information to the wearer. The information can include at least two options for selection. The wearable apparatus can also include a brain monitor configured to track brain wave activity of the wearer. The apparatus can further include a processor configured to identify one of the at least two options as selected based on the brain wave activity tracked by the brain monitor.

21 Claims, 10 Drawing Sheets

(56) References Cited

U.S. PATENT DOCUMENTS

| | | | |
|---|---|---|---|
| 2015/0313496 A1* | 11/2015 | Connor | A61B 5/6814 |
| | | | 600/301 |
| 2015/0338917 A1* | 11/2015 | Steiner | A61B 5/316 |
| | | | 345/156 |
| 2016/0038770 A1* | 2/2016 | Tyler | A61N 7/02 |
| | | | 601/2 |
| 2016/0109851 A1* | 4/2016 | Tsang | G06F 1/163 |
| | | | 359/9 |
| 2016/0187654 A1* | 6/2016 | Border | G02B 5/18 |
| | | | 359/567 |
| 2016/0239084 A1* | 8/2016 | Connor | G06F 3/015 |
| 2017/0188947 A1* | 7/2017 | Connor | A61B 5/291 |
| 2017/0249009 A1* | 8/2017 | Parshionikar | G06K 9/00315 |
| 2017/0259167 A1* | 9/2017 | Cook | A63F 13/28 |
| 2017/0322679 A1* | 11/2017 | Gordon | G06N 20/00 |
| 2017/0340230 A1* | 11/2017 | Hasegawa | A61B 5/291 |
| 2018/0280656 A1* | 10/2018 | Cole | A61M 21/00 |
| 2018/0364810 A1* | 12/2018 | Parshionikar | G06F 3/012 |
| 2019/0196585 A1* | 6/2019 | Laszlo | A61B 5/38 |
| 2019/0377477 A1* | 12/2019 | Haist | G06F 3/017 |
| 2020/0170534 A1* | 6/2020 | Flaeschner | A61B 5/316 |
| 2020/0192478 A1* | 6/2020 | Alcaide | G06F 3/015 |
| 2020/0249752 A1* | 8/2020 | Parshionikar | G06F 1/163 |

\* cited by examiner

APPARATUS AND METHOD FOR USER INTERFACING IN DISPLAY GLASSES

BACKGROUND

The disclosure relates generally to display technologies, and more particularly, to user interfacing in display glasses.

Wearable electronic glasses provide enhancements to users' lives in a variety of ways. These enhancements may improve user experience in a wide range of applications, from factory floor usage by workers on a parts assembly project to gaming and other recreational activities. Numerous other applications of wearable electronic glasses are possible.

SUMMARY

The disclosure relates generally to display technologies, and more particularly, to user interfacing in display glasses.

A wearable apparatus for display glasses, according to certain embodiments, can include a display that includes a pair of screens configured to be mounted in front of respective eyes of a face of a wearer of the apparatus. The display can be configured to provide a display of information to the wearer. The information can include at least two options for selection. The wearable apparatus can also include a brain monitor configured to track brain wave activity of the wearer. The apparatus can further include a processor configured to identify one of the at least two options as selected based on the brain wave activity tracked by the brain monitor.

In certain embodiments, a wearable apparatus for display glasses can include a display that includes a pair of screens configured to be mounted in front of respective eyes of a face of a wearer of the apparatus. The display can be configured to provide a display of information to the wearer. The information can include at least two options for selection. The wearable apparatus can also include an electromyograph device configured to track muscle activity of the wearer. The wearable apparatus can further include a processor configured to identify one of the at least two options as selected based on the muscle activity tracked by the electromyograph device.

BRIEF DESCRIPTION OF THE DRAWINGS

The embodiments will be more readily understood in view of the following description when accompanied by the below figures and wherein like reference numerals represent like elements, wherein.

DETAILED DESCRIPTION

Figure 1:
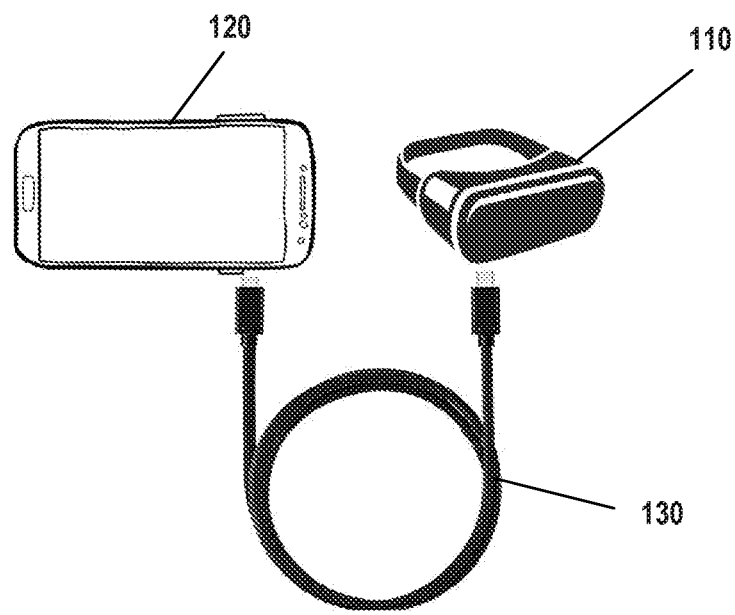
FIG. 1 illustrates an example of hardware consistent with certain embodiments of the present disclosure.

In the following detailed description, numerous specific details are set forth by way of examples in order to provide a thorough understanding of the relevant disclosures. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure.

Throughout the specification and claims, terms may have nuanced meanings suggested or implied in context beyond an explicitly stated meaning. Likewise, the phrase "in one embodiment/example" as used herein does not necessarily refer to the same embodiment and the phrase "in another embodiment/example" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

As will be disclosed in detail below, among other novel features, the display system and method thereof disclosed herein may provide the ability to enhance the user interfacing and the security of the display system. User interfacing and security enhancements according to certain embodiments of the present disclosure may benefit wired and wireless displays. For example, certain embodiments may benefit wearable electronic glasses that are connected to a smart phone or other devices. Likewise, certain embodiments of the present disclosure may benefit wearable electronic glasses that lack a physical keyboard, mouse, or the like, or in cases where the physical keyboard, mouse, or the like may not be conveniently located at all times.

Additional novel features will be set forth in part in the description which follows, and in part will become apparent to those skilled in the art upon examination of the following and the accompanying drawings or may be learned by production or operation of the examples. The novel features of the present disclosure may be realized and attained by practice or use of various aspects of the methodologies, instrumentalities, and combinations set forth in the detailed examples discussed below.

Wearable electronic glasses can fall into a variety of categories. A first category of wearable electronic glasses is simple display glasses. Simple display glasses can provide a two-dimensional or three-dimensional image. Simple display glasses may not take into account user motion, but simply display a still image or video image. Simple display glasses can have varying levels of hardware.

A second category of wearable electronic glasses is virtual reality (VR) glasses. VR glasses may take into account the position and orientation of a user's head in the display process. Thus, for example, VR glasses may display a particular portion of a still panoramic image depending on the angle of the user's head. VR glasses can also be used in connection with three-dimensional (3D) images or videos to create a realistic and immersive user experience.

A third category of wearable electronic glasses is augmented reality (AR) glasses. AR glasses may combine live images of reality with computer-based enhancements. For example, the user may see a live video image of their current field of view (FOV) with additional data superimposed over the image.

The same hardware device may be configured in a variety of ways. For example, glasses with a built-in camera and posture and/or motion detection may function as simple display glasses in one application, as VR glasses in another application, and as AR glasses in yet another application. Accordingly, it may be imprecise to speak of a particular hardware device exclusively as simple display, VR, or AR. Nevertheless, the term "display glasses" may broadly encompass simple display glasses, VR glasses, and AR glasses, regardless of their specific mode of use.

In certain cases, the motion detection may be distributed away from the glasses themselves. For example, an associated device may observe the glasses using one or more cameras and may detect motion based on the analysis of captured images.

Other categories of wearable electronic glasses also exist. For example, wearable electronic glasses can be designed to be used by one eye or two eyes. Additionally, wearable electronic glasses may be self-contained or may operate in connection with another device. Connected operation may permit some of the processing to be handled by another device, which may reduce the processing requirements on the wearable electronic glasses.

Connected operation wearable electronic glasses can be further sub-divided into wired and wireless wearable electronic glasses, or wired-mode and wireless-mode, for wearable electronic glasses that are capable of both modes. The use of a wireless connection may have value, particularly when the wearable electronic glasses are connected to a smart phone or similar portable device.

FIG. 1 illustrates an embodiment according to the present disclosure. As shown in FIG. 1, a system can include display glasses 110 connected to a smart phone 120 by a cable 130. The smart phone 120 is an example of any desired device, such as any portable electronic device. The cable 130 can be provided with suitable connectors. For example, universal serial bus (USB) type C connectors may be used, although other connector types may be used in other applications. The display glasses 110 can operate as virtual display glasses without requiring any internal CPU, control system, or even battery.

Figure 3:
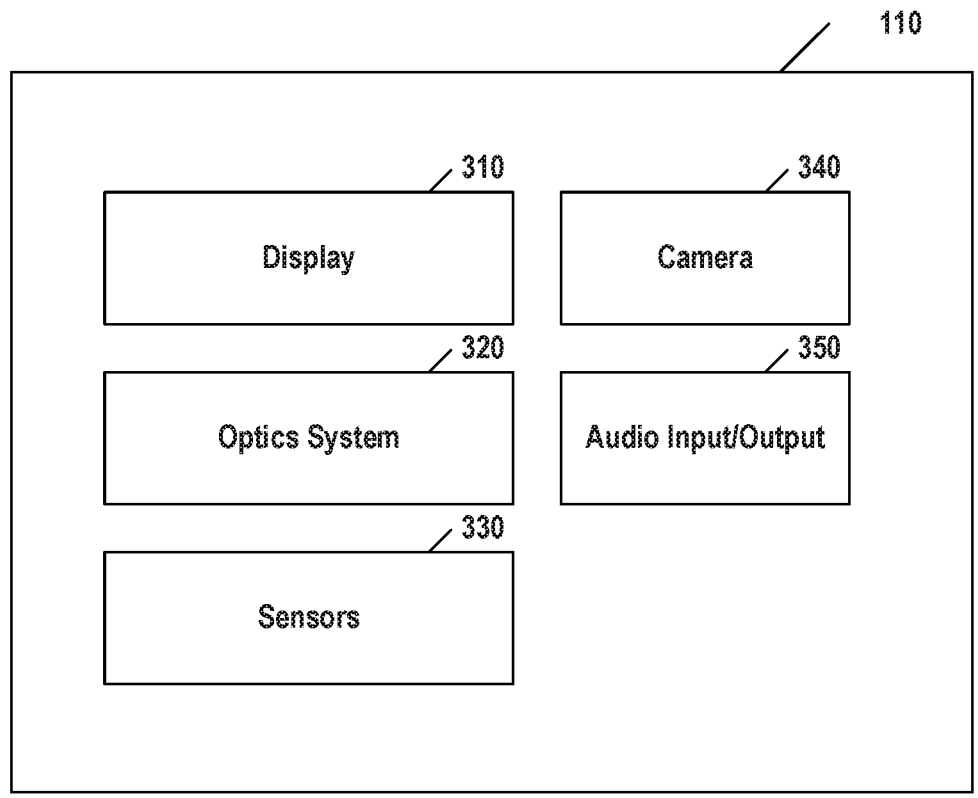
FIG. 3 illustrates a system according to certain embodiments of the present disclosure.

FIG. 3 illustrates an embodiment of display glasses consistent with certain embodiments of the present disclosure. As shown in FIG. 3, The display glasses 110 may include a display 310, such as a micro-OLED display. The display glasses 110 may also include an optics system 320, which may include a lens, such as a birdbath and/or freeform lens and a waveguide.

The display glasses 110 may also include sensors 330. The sensors 330 may be, for example, 6 DOF MEMS G-Sensors. The display glasses 110 may also a camera 340 and audio input/output 350, which may be a built-in earphone/microphone or a jack or other interface for external audio devices. Other audio options are also possible, such as one or more built-in speaker or wireless connection to wireless headphones or earbuds.

As will be disclosed below, the sensors 330 may also include other sensor types, including cameras, infrared cameras, sonic sensors, ultrasonic sensors, electroencephalogy electrodes, electromyogram electrodes, and the like. A microphone may also be used as one of the sensors 330.

When a microphone is used as a sensor, a processor of the system may be configured for speech recognition, voiceprint identification, or other audio-based processing. For example, a wearer may blow into or across a microphone to activate a function. Likewise, the processor may use the microphone to observe and process whistles, clicks, claps, or other audio signals from the wearer of the display glasses.

Figure 2:
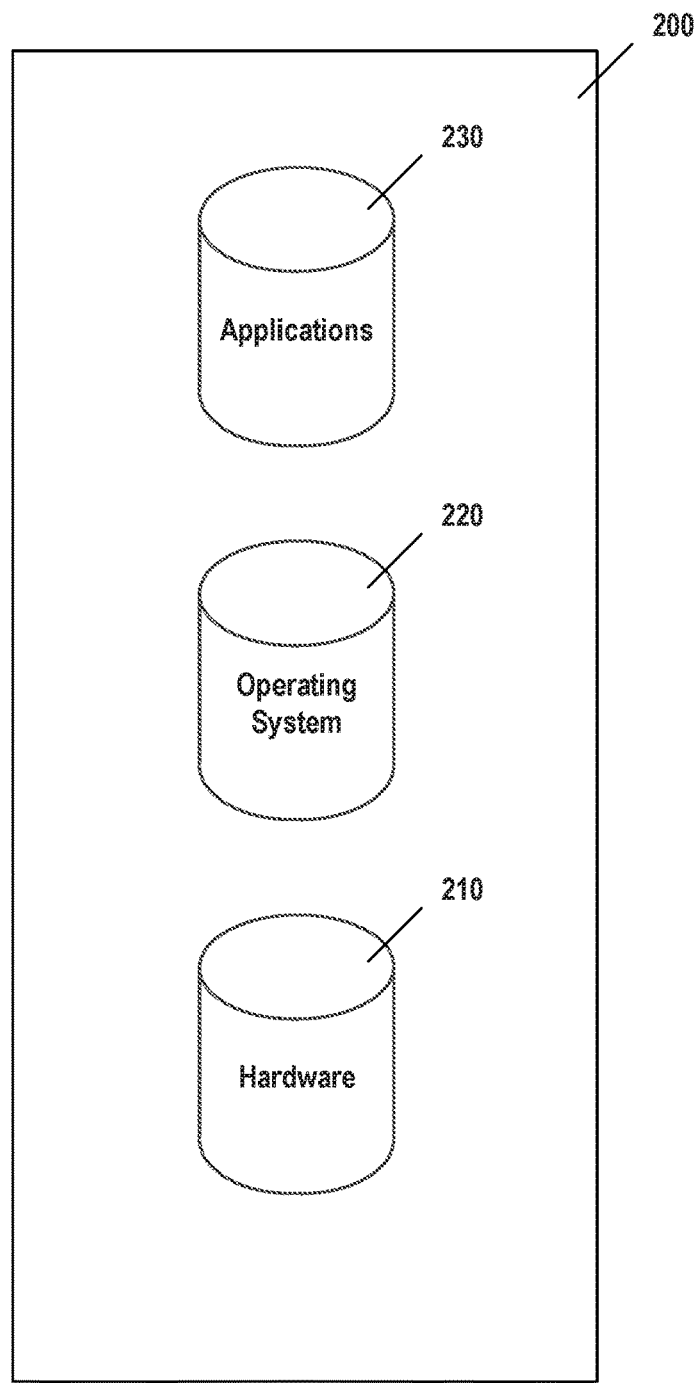
FIG. 2 illustrates an architecture of certain embodiments according to the present disclosure.

FIG. 2 illustrates an architecture of certain embodiments according to the present disclosure. As shown in FIG. 2, a system 200 for display glasses may involve multiple layers. At the conceptual bottom of the stack, there may be hardware 210, such as a monocular or binocular display, motion sensors, processors, and the like. This hardware 210 may be equipped with an operating system 220, which may permit the use of the hardware 210 in numerous ways. Applications 230 may form a conceptual top layer and may provide the specific ways in which the operating system 220 is used to control and access the hardware 210.

Display glasses may have numerous applications 230. For example, display glasses can be configured in hardware 210 with a wide field of view (FOV), such as fifty degrees or more. The display glasses connected to a smart phone may permit the user to use the smart phone's user interface features, in application 230 running on operating system 220, for adjustments to volume, dimming, and so on. For example, software installed on the smart phone may permit swiping, pinching, or other gestures on the touch interface to perform control actions for a movie being displayed on the display glass screen. In this example, hardware 210, operating systems 220, and applications 230 may be present both at the smart phone and also at the display glasses. Thus, system 200 is illustrated as a single box, but may span multiple devices.

Another application 230 may be gaming. In this context, the user interface of the smart phone may serve as a game controller. In a further application, the display glasses can be used for a virtual computer monitor array. In this example, the smart phone may serve as a CPU, and the smartphone's user interface may serve as a touchpad or mouse. A wireless keyboard can be connected to the smart phone to provide a more extensive set of keys. As a further option, the smart phone's camera can be used to monitor the finger position of the user on an arbitrary surface, to thereby provide a virtual keyboard. Thus, additional hardware 210, such as peripherals, accessories, and the like, can also be provided.

Figure 4:
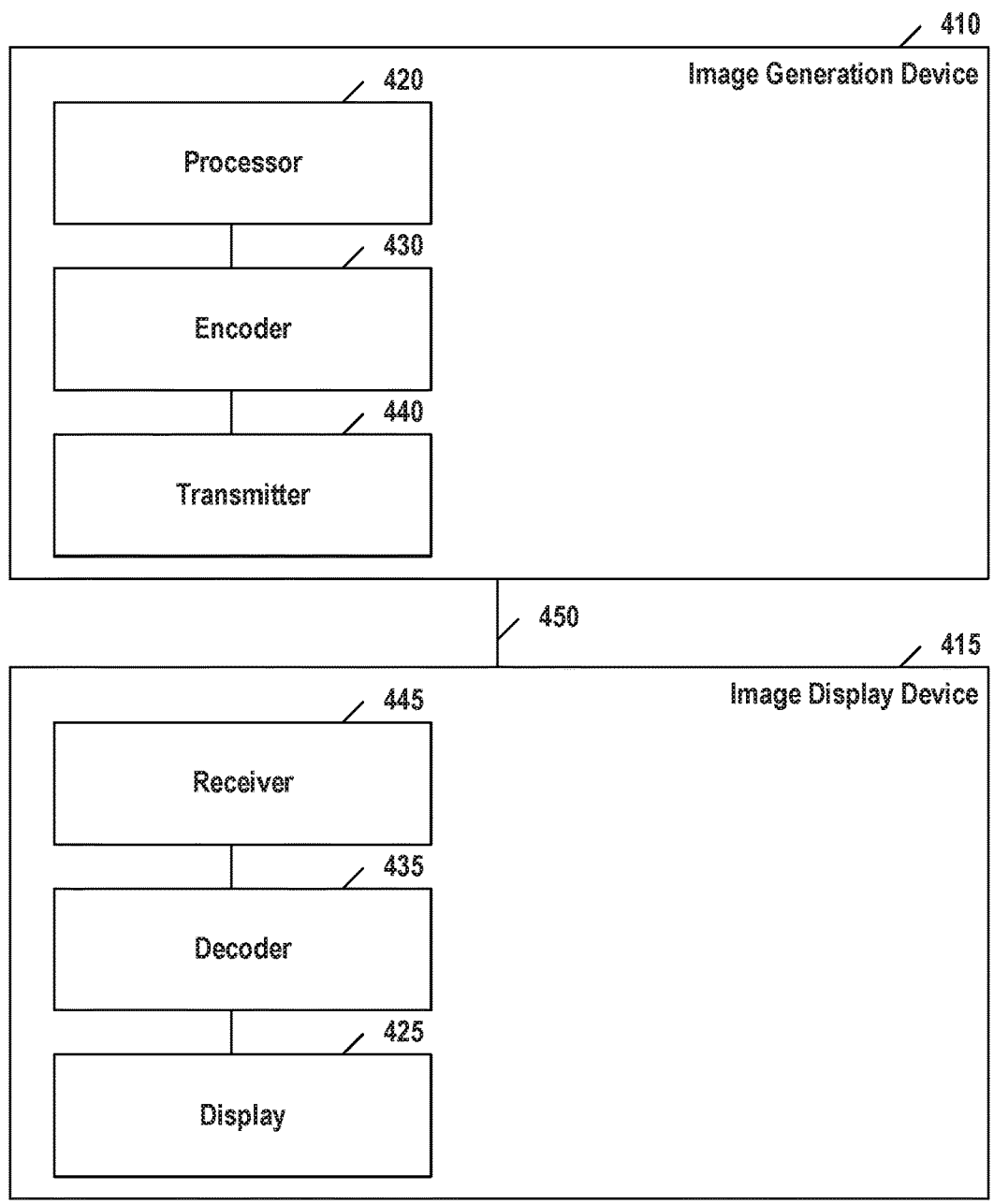
FIG. 4 illustrates a system according to certain embodiments.

FIG. 4 illustrates a system according to certain embodiments. As shown in FIG. 4, there can be an image generation device 410, such as a smart phone, and an image display device 415, such as display glasses.

The image generation device 410 may include a processor 420 configured to generate images. The processor 420 may, for example, be a CPU or graphics processing unit (GPU). The image generation device 410 may include multiple processors, and processor 420 may include multiple cores. For example, in a binocular implementation, there may be one graphics processor, graphics processing core, or processing thread configured to generate left-eye images, and similarly, another of the same configured to generate right eye images. The processor 420 may generate an image or video stream by combining multiple input streams from other sources. For example, combining can include combining left and right eye images, combining a video with overlaid data, or the like. Other options are also permitted.

The image generation device may also include an encoder 430 configured to secure the output of processor 420. Example embodiments of the encoder 430 are discussed below. The output of the encoder 430 may be provided to a transmitter 440. The transmitter 440 may be a wireless transmitter or a wired transmitter, including a port for a cabled connection, such as a universal serial bus (USB) connection or video graphics array (VGA) connection. Wireless transmitters may include relatively low power transmitters, such as those following Bluetooth standards, or higher power transmitters, including WiFi or broadcast television transmitters.

Transmitter 440 may provide the encoded signal (optionally further encoded for communications purposes) over connection 450 toward image display device 415. Although connection 450 is shown as a direct one-to-one connection, any other connection mechanism is permitted. For example, multi-cast or broadcast techniques may be used, and the signal may be relayed using, for example, repeater stations.

Data, for example, encoded data sent over connection 450, may be received at the image display device 415 and particularly by the receiver 445. The receiver 445 may be a standard receiver of the kind that corresponds to the transmission mechanism used by transmitter 440. The output of receiver 445 may be provided to decoder 435, which may remove the encoding and provide usable image and/or video data to display 425. The decoder 435 will be discussed in more detail below. The display 425 may be, for example, an OLED display, such as an AMOLED display.

The encoder 430 and decoder 435 may be variously embodied and configured. For example, the decoder 435 may be configured to decode using a key stored in memory (not illustrated) of the image display device 415. The image generation device 410 may be configured to control the encoder 430 to encode the data based on the key.

One way to implement this keyed approach is for the image display device 415 to have a permanent and unalterable key, which can be read in a human-readable form on an exterior surface of the image display device 415. A user can then input this key to the image generation device 410. Similarly, a printed QR code or bar code on the image display device 415 could be read by a camera of the image generation device 410. Other key exchange options are also possible, such as permitting the image display device 415 to transmit its own key wireless in response to a button press on the image display device 415 itself. In a further embodiment, the image display device 415 may be a wearable device that guides a wearer through a configuration sequence to calibrate motion sensor(s) of the image display device 415. The wearable device may signal its own key to the image generation device 410 upon the successful completion of the configuration sequence.

In another approach, the image generation device 410 may request access to the key, and the wearer of the display glasses may provide access to the key through a responsive detectable gesture, such as nodding the wearer's head, blinking the wearer's eyes, or the like. Further discussion of eye tracking of the wearer's eyes may be found below with reference to FIG. 6, for example.

In another approach, the decryption key may be an acquired key. For example, display glasses may receive the key in response to payment, in response to entering a password, or in response to passing a biometric test. The biometric test may be performed using a brain monitor, muscle monitor, eye monitoring camera, or the like. Other options are also possible. For example, a key fill port may be provided on the image display device 415, and the key may be temporarily loaded into memory from the key fill port.

Other options are also possible. For example, landmarks disposed on an exterior surface of the image display device 415 may be detected by a camera, for example, a front camera, of the image generation device 410. This detection may confirm that the image display device 415 is in the vicinity of the image generation device 410.

In certain embodiments, the key may be a time-varying pseudorandom code displayed on the image display device 415, for example, at startup. Thus, for example, a wearer may be shown a key in the field of view of the display glasses, and the wearer may enter that key into a smartphone to begin the encoded transmission of data. Similarly, the key may be presented in a machine-readable format on the display 425, and a camera of the image generation device 410 may be used to read the key.

Figure 5:
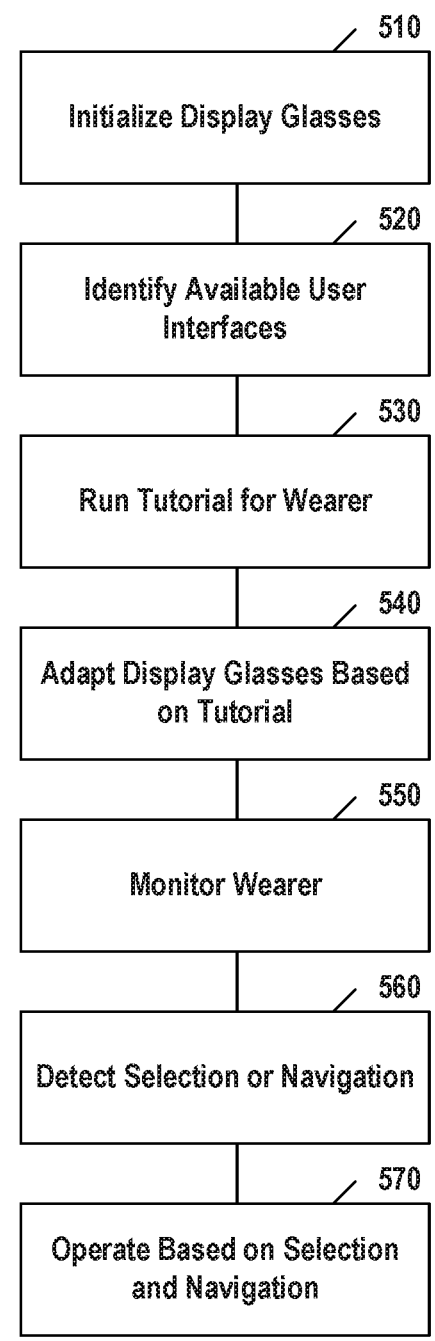
FIG. 5 illustrates a method according to certain embodiments.

FIG. 5 illustrates a method according to certain embodiments. The method of FIG. 5 may be performed by any of the apparatuses or systems described herein. As shown in FIG. 5, a method 500 can include, at 510, initializing display glasses. Initialization can be performed at power-on of the display glasses. The initialization process may include a series of tests of the hardware and/or software of the display glasses. As part of, or after, the initialization, at 520, the display glasses can identify available user interfaces. The available user interfaces may be interfaces made possible by hardware and/or software of the display glasses themselves, as well as user interfaces available in an associated device, such as a smart phone, or a remote device, such as a nearby computer, television, a smart speaker, or other usable device. Identified user interfaces may include a brain monitor, muscle monitor, eye tracker or other eye camera, motion sensors within the display glasses themselves, as well as motion sensors of other devices, such as smart watches.

At 530, the method 500 can include running a tutorial for the wearer. Running a tutorial for the wearer may allow the wearer to become familiar with all of the available user interfaces. Additionally, the tutorial may allow the wearable device to become familiar with the wearer. The tutorial may be configured as a series of configurations to set up, as a game to be played, or may be presented in a straightforward manner as a tutorial. During the tutorial, the wearable device may gather information regarding the wearer of the device as well as the operational status of the available user interfaces. For example, the wearable device may learn the voice of the wearer, the wearable device may recognize brain wave patterns of the wearer, and the wearable device may recognize muscle movement patterns of the wearer.

At 540, the display glasses may be adapted or may adapt themselves based on the tutorial. For example, if one or more of the user interfaces was not able to recognize reliable data, it may be temporarily disabled or may remain in a learning mode as opposed to a full use mode. Likewise, if a wearer selects to disable one or more user interface during the tutorial, the user interface may be disabled by the wearer's selection.

At 550, the display glasses may monitor the wearer through each of the active user interfaces. For example, a brain monitor may monitor the brain waves of a wearer, a muscle monitor may monitor muscle activation and/or deactivation of the wearer, and an eye tracker may monitor eye position and open/shut status of the wearer.

At 560, the display glasses may detect selection or navigation by the wearer. For example, an eye-tracking interface may detect a region of the display as being currently pointed at, and a muscle monitor may detect that a selection is being made at that navigation point. In certain embodiments, navigation plus dwell time exceeding a certain threshold may be interpreted as a selection. Thus, if a cursor is navigated to hover over a selection option for a certain minimum amount of time, the option may be selected. As another example, if a wearer's eyes are tracked to the left edge of the screen for a minimum dwell time, the system may go back a screen, while if the wearer's eyes are tracked to the right edge of the screen for a minimum dwell time, the system may go forward a screen.

At 570, the display glasses may operate based on the selection and/or navigation. For example, the display glasses may move from a first screen to a subsequent screen or may run a process based on the selection and/or navigation.

Figure 6:
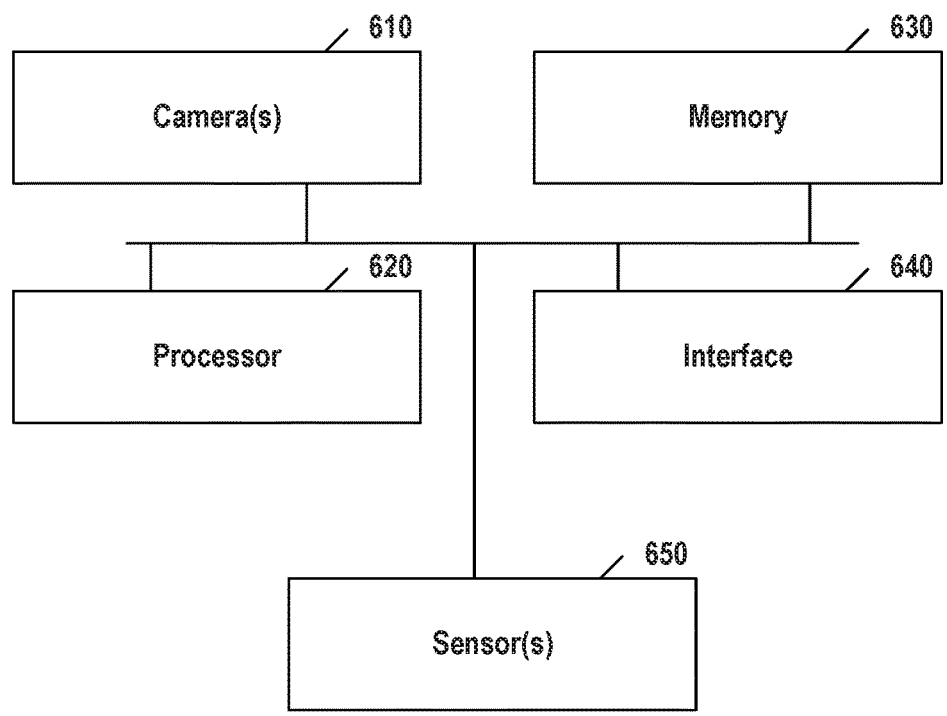
FIG. 6 illustrates an eye-tracking sub-system according to certain embodiments of the present disclosure.

FIG. 6 illustrates an eye-tracking subsystem 600 according to certain embodiments of the present disclosure. As shown in FIG. 6, the eye-tracking subsystem 600 may include one or more camera(s) 610. The camera(s) 610 may be visible wavelength cameras, such as cameras suitable for performing retina scans or eye-print identification. Additionally, or alternatively, the camera(s) 610 may be infrared cameras, which may be able to track the eyes open/shut status of the wearer's eyes or the pupil position of one or more of the wearer's eyes.

The camera(s) 610 may be internal to display glasses or external to the display glasses. For example, the camera(s) 610 may be installed in the interior of a vehicle and may be assigned to multiple monitoring tasks, including observing driver alertness, passenger occupancy, or the like. Likewise, the camera(s) 610 may be installed in the frame of a laptop, computer monitor, or television and may be assigned to multiple tasks including user authentication, video chatting, or the like. Other implementations are also possible.

As mentioned above, the camera(s) 610 may be installed internal to the display glasses. For example, when an image is projected onto the glasses from an imaging device, the camera(s) 610 may be provided adjacent to or near the imaging device. The camera(s) 610 may, in such a case, observe a reflection of the wearer's eyes from a reflective surface of the display glasses. For example, an infrared reflective film may be provided on an interior surface of the display glasses, which may not significantly affect viewing, but which may permit an infrared reflection of the wearer's eyes to be visible to camera(s) 610 operating in the infrared range.

Likewise, in certain embodiments, the camera(s) 610 may be installed with a direct line of sight to the wearer's eyes, such as embedded in a frame of the wearer's glasses. Thus, for example, one lens with a wide viewing angle may be placed at a bridge or top bar of the display glasses. As another alternative, independent cameras of camera(s) 610 may be placed near the periphery of a corresponding lens of the display glasses.

When the camera(s) 610 are used for eye-tracking, the eye-tracking subsystem 600 may take advantage of the ordinary correlation between left eye and right eye movement. Thus, for example, the eye-tracking subsystem 600 may, for example, only include one camera and may only track one eye of the wearer. This approach may assume that the wearer has at least an eye on the side monitored by the camera and that the wearer is not experiencing significant amblyopia in that eye. To maximize a served wearer population, camera(s) 610 may be positioned to monitor both eyes, thereby permitting use by wearers with only one eye or with significant amblyopia in one eye.

The camera(s) 610 internally mounted in the display glasses may be used for additional tasks in addition to eye-tracking. For example, the camera(s) 610 may be used for user authentication using biometric data about the wearer, such as skin color, lash thickness or length, eye size, position, color, shape, iris, and/or retina appearance. The camera(s) 610 can also be used to monitor wearer alertness, responsiveness, or the like. For example, by observing eyelid position and/or pupil position over time, this or another sub-system may determine that a wearer has become drowsy or is sleeping.

In case camera(s) 610 detect that the wearer is drowsy, the glasses may be disabled, or any existing authentication may be disabled. Such an approach may help to protect a user's sleep and to prevent accidental usage of any features that require authentication. In certain embodiments, the display glasses may be used to help a wearer fall asleep. In such a case, as the wearer's eyes show signs of drowsiness, audio levels and visual brightness may be lowered to aid in the wearer falling asleep.

Camera(s) 610 may be configured to perform eye tracking as well as other tasks. For example, in certain embodiments camera(s) 610 may be able to observe a greater portion of the wearer's face and may be able to observe facial expressions. For example, the camera(s) 610 may be able to observe blinking, winking, raised eyebrows, or smiling with the eyes. Smiling with the eyes can refer to the aspect of smiling in which the corners of the eyes are drawn slightly together, which can result in so-called "crow's feet" wrinkles at the corners of the eyes.

Camera(s) 610 are an example of a sensor system that can be used to, among other things, track eye movement. Eye movement can also be tracked in other ways. For example, there is often some correlation between head movement and eye movement. Thus, motion detection of the display glasses can be used to confirm and/or provide an estimation of eye movement.

Another option is to monitor the muscles that move the eyes. In humans, the movement of each eye is controlled by six muscles in three pairs: the superior and inferior rectus, the lateral and medial rectus, and the superior and inferior oblique. In certain embodiments, these muscles or a subset of them may be monitored to infer eye movement. Monitoring may be performed using surface or subdermal electrodes. Broadly, any electromyography device, or electromyograph (EMG) may be used to detect muscle movement, broadly including eye movements and other muscle movements.

For example, the EMG may be configured to measure jaw muscles, cheek muscles, or the like. The jaw muscle activation or deactivation may be detected by the EMG. The EMG measurement may be triggered or assisted by the use of a microphone that may detect teeth gritting and/or grinding. Thus, for example, when a wearer of the display glasses grits or grinds the wearer's teeth, the muscle or nerve activity associated with this action by the wearer may be detected by the EMG, by the microphone, or by both working in combination with one another.

Jaw muscle activation or deactivation can be variously monitored in addition to the EMG. For example, a bite guard or the like may be provided with pressure sensors and may be inserted into the wearers mouth. This bite guard may provide a further way of sensing user input.

Regardless of how the jaw muscle activation or deactivation is detected, the detected jaw muscle activation may be used in various ways. For example, a processor may count a number of consecutive jaw muscle activations and may trigger different actions depending on the number of consecutive jaw muscle activations. Thus, for example, one jaw muscle activation may be treated as a single mouse click, two jaw muscle activations may be treated as a double-click, and so on. In another example, the user interface may switch between options depending the jaw muscle activation. For example, if the jaw muscle is activated a first option may be selected, while the jaw muscle is deactivated, a second option may be selected. In a further example, a jaw muscle activation may be used to switch to a next option, such as to switch to a different option from a list of options. In this way, a series of jaw muscle activations may be used to scroll through a list of options.

Jaw muscle activation and deactivation monitoring is one possible use of EMG. On the other hand, other muscles may also or alternatively be monitored using EMG. Thus, similar techniques to those described above may be used with respect to other muscles.

In certain embodiments, the output of the EMG may be monitored by a learning network. The learning network may use UI selections obtained through muscular movement, such as mouse clicks, keypad operation, gestures, or the like, to learn the detection of those muscular movements. Thus, for example, a trained neural network may receive an output of an EMG and may determine a corresponding muscular movement, such as a double-click of a left mouse button, a keypress and depress, or a hand gesture, such as a swipe, pinch, or the like.

The bite guard mentioned above may, in certain embodiments, provide a truth basis for a neural network to observe muscle activation. Other supplemental tools, such as a physical keyboard, a physical mouse, or physical joystick, may similarly serve as a truth basis for the neural network. During an initial period, the neural network may be trained while the wearer is using the supplemental tool. Once the neural network is adequately trained, the supplemental tool may be omitted.

The neural network may also be trained to distinguish between muscular activation used to bite or release and muscle activation used to grind: for example, muscle motion used to move the lower mandible left and right. A processor may treat different jaw muscle activations differently, depending on whether a bite, grind, or combination thereof is detected. For example, a bite may be treated as a left mouse click, while a grind may be treated as a right mouse click. Optionally, the processor and/or neural network may estimate current mandible position based on EMG output. A camera in the display glasses or otherwise facing the wearer may be used to provide a truth basis for the estimate. The position of the mandible may be tracked to serve as a pointer. In effect, the wearer's mandible may serve as a joystick for controlling a cursor on a screen of the display glasses. Predetermined periods may be used to determine whether two single clicks or one double click is detected. The predetermined period may be user-configurable: for example, a user may select to count two jaw muscle activations as a double click if they occur in less than one second, less than half a second, or within two seconds. These are just example values. Similarly, the cursor may be deemed to be hovering over an option if a dwell time over the option exceeds a threshold, such as one second, two seconds, or the like. This threshold may also be configurable by a user.

In certain embodiments, upon first use of the display glasses by a given wearer, the system may lead the given wearer through a tutorial, which may be used to train the neural network based on pre-determined motions of the wearer. The wearer may be instructed to make various gestures, and the EMG may measure nerve activity associated with the muscular activation/deactivation of the wearer associated with the various gestures. The gestures may include hand gestures but may also include facial gestures, such as clenching the wearer's jaw, relaxing the wearer's jaw, gritting the wearer's teeth, grinding the wearer's teeth, or the like.

In certain embodiments, the EMG may be used in connection with a microphone and a neural network. For example, the wearer may be instructed to speak certain words, phrases, sentences, or the like aloud. The neural network may learn what muscles are used for which words, phrases, sentences, or the like by aligning the audio through the microphone with EMG sensor output. The wearer may then be instructed to simply mouth or whisper the same words, phrases, or sentences, and the neural network may be able to identify the words, phrases, or sentences based only the EMG sensor data. In this way, certain embodiments of the present disclosure may provide a form of silent voice recognition as an additional user interface technology.

In certain embodiments, the display glasses may include sensors along the temples, bridge, top bar, pads, lenses, or other elements thereof. These sensors may monitor muscles of the face. For example, any of the following muscles may be monitored in any combination: *frontalis*, corrugator *supercilia, procerus*, depressor *supercilia*, orbicularis *oculi* (superior lateral and/or lateral), *nasalis*, levator labii *superioris* alaeque nasi, levator labii *superioris*, zygomaticus *minor*, zygomaticus *major*, orbicularis *oris, buccinator, risorius*, masseter, depressor *anguli oris*, depressor labii inferioris, *platysma*, or *mentalis*.

Other technologies are also permitted. For example, sonic or ultrasonic sensors may be used to identify the position of an eye. Eye movement may also be indirectly tracked using a brain monitor, as discussed below with reference to FIG. 7.

As shown in FIG. 6, the eye-tracking subsystem 600 may also include a processor 620. The processor 620 may be any suitable computing device, such as a general-purpose processor running software, or an application-specific integrated circuit. The eye-tracking subsystem 600 may also include a memory 630, which may be any desired mechanism for storing data either temporarily, such as in a buffer, or for longer periods of time, such as in storage. The eye-tracking subsystem 600 may also include an interface 640 for providing communication and interaction with other sub-systems.

The eye-tracking subsystem 600 may also include other sensor(s) 650. The other sensors may include a microelectromechanical system (MEMS) motion sensing device, a gyroscopic motion sensor, or the like. Other sensor types, such as sonic or ultra-sonic sensors may also be included. Additional sensor types, such as brain monitoring devices, may additionally be included, as discussed below in more detail with reference to FIG. 7.

Figure 7:
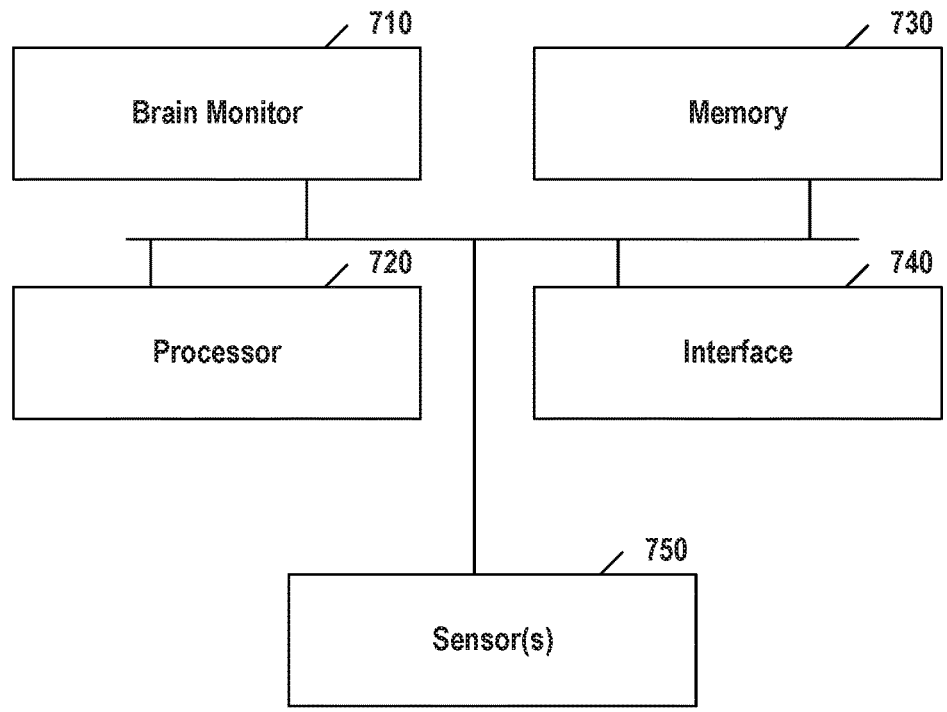
FIG. 7 illustrates a brain monitoring sub-system according to certain embodiments.

FIG. 7 illustrates a brain monitoring sub-system 700 according to certain embodiments. As shown in FIG. 7, a brain monitor 710, such as an electroencephalogram (EEG) device, may be provided. The EEG device may produce an EEG in response to monitoring brain activity. The EEG device may include electrodes that contact a wearer's scalp. The EEG produced by the EEG device may also be referred to as a record of the brainwaves of the wearer. Thus, the brain monitor 710 may also include a brainwave headset. The brain monitor 710 may be variously embodied as a headband, a crown, a cap, or any other desired structure.

The brain monitoring sub-system 700 may also include other sensor(s) 750, such as any of the sensors described above. For example, an EMG device may be provided as one of the sensor(s) 750. The brain monitoring sub-system 700 may also include a processor 720 and memory 730. The processor 720 and memory 730 may process data from the brain monitor 710 and optionally may combine this data with data from sensor(s) 750. The processor 720 and memory 730 may implement a machine learning or other artificial intelligence system.

For example, in certain embodiments, a wearer may be instructed to move the wearer's hands one way to indicate "yes" and a different way to indicate "no." The brain monitor 710 may determine the wearer's EEG and possibly EMG or other biosensor data and may generate a signal corresponding to "yes" or "no" based on the wearer's hand movements.

Although EEG is mentioned as one form of brain monitoring, other methods of brain monitoring are also permitted, including magnetoencephalography (MEG) and functional magnetic resonance imaging (fMRI). References to EEG may broadly also include event-related potentials (ERP) approaches. In certain embodiments, the electrodes used for measuring ERP or EEG may also be used for other purposes, such as for transcranial direct current stimulation (tDCS) or any other form of transcranial electrical stimulation (TES).

The processor 720 and memory 730 may embody a trained neural network. Moreover, the neural network may learn from reinforcement training with a specific wearer. In certain embodiments, the neural net may learn to identify the specific muscular action of the wearer based on brain wave data alone or brain wave data in combination with other sensor data.

A neural network, generally speaking, may provide a non-linear function parameterized by weights, such that the function can, in some sense, be changed by changing the weights. A loss function can be used to evaluate how well a neural network functions for a given task. Loss can be considered the square of the difference between a desired output and an actual output. Ideally, the loss would be zero in every case. Realistically, a loss function will be non-zero, as perfection may be unachievable. In general, the larger the loss function, the worse the performance of the neural network.

When a neural network is first created, the weights can be initialized randomly. Under such circumstances, the loss may be high. Training can be used to improve the loss to a lower value. A gradient descent approach can be used to minimize loss. There are various modifications of the gradient descent approach that can be used, sometimes referred to as mini-batch gradient descent or stochastic gradient descent.

A tutorial may request a wearer of the wearable device to perform a series of activities. These activities may have known values, and consequently may serve as training data to train a neural network. The neural network may be pre-trained so that the neural network is not initialized from completely random weights, but learning can still be used to fine-tune the neural network to the particular wearer.

Depending on the quality of the brain monitor 710, the neural network of the brain monitoring sub-system 700 may learn to distinguish not only gross motor movements but also fine motor movements. Thus, for example, the brain monitoring sub-system 700 may learn to identify the intended keystrokes of a wearer's fingers.

Certain embodiments may provide interaction between the brain monitor 710 and the display glasses. For example, the display glasses may display a keyboard and a representation of the wearer's hands. The wearer may then operate the displayed keyboard as though it were a real keyboard, while the brain monitor 710 identifies the movements of the wearer's fingers from brain waves of the wearer.

The brain monitoring sub-system 700 may also be configured to predict the wearer's selections. For example, by monitoring and learning from previous decisions by the wearer, a neural network of the brain monitoring sub-system 700 may be able to accurately predict a wearer's selection prior to the wearer making the selection. This predictive power may be used to pre-load and/or pre-run instructions or to pre-fetch other data as predicted will be desired by the wearer.

In certain embodiments, the brain monitor 710 may be built into one or both temples of the display glasses. Other implementations are also possible. For example, the brain monitor 710 may be embodied as a separate crown or cap that is worn in addition to the display glasses. In such a case, the interface 740 may provide a wireless interface to the display glasses.

Although EEG and EMG devices have been discussed above, other biosensors may similarly be used. For example, an electrocardiogram (ECG) device may be employed to supplement the information provided by other sensors.

Figure 8:
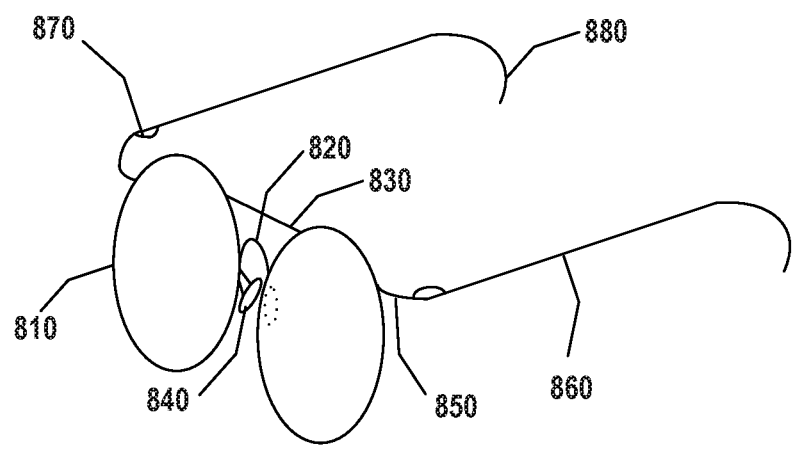
FIG. 8 illustrates display glasses according to certain embodiments.

FIG. 8 illustrates display glasses 800 according to certain embodiments. As shown in FIG. 8, display glasses 800 can include lenses 810, which may be screens (for example, LED or OLED screens) or inwardly reflective mirrors rather than conventional lenses. The lenses 810 may be connected to one another by a bridge 820 and top bar 830.

The lenses 810 may be supported by a wearer's nose using pads 840 or a saddle structure (not shown). The lenses 810 may also be supported by the wearer's ears using end pieces 850 connected to temples 860 via hinges 870. Temple tips 880 may help to secure the display glasses 800 to a wearer's ears.

Features such as a processor, memory, camera, and so on are not shown in FIG. 8 but may be discretely located within or behind any of the illustrated features. The display glasses 800 may also include, although not shown in FIG. 8, a cowl, skirt, or other baffle configured to reduce light to the wearer's eyes from other sources. The display glasses 800 may also include, although not shown in FIG. 8, a complete crown, cap, or helmet configured to be positioned around or over a wearer's head.

Figure 9:
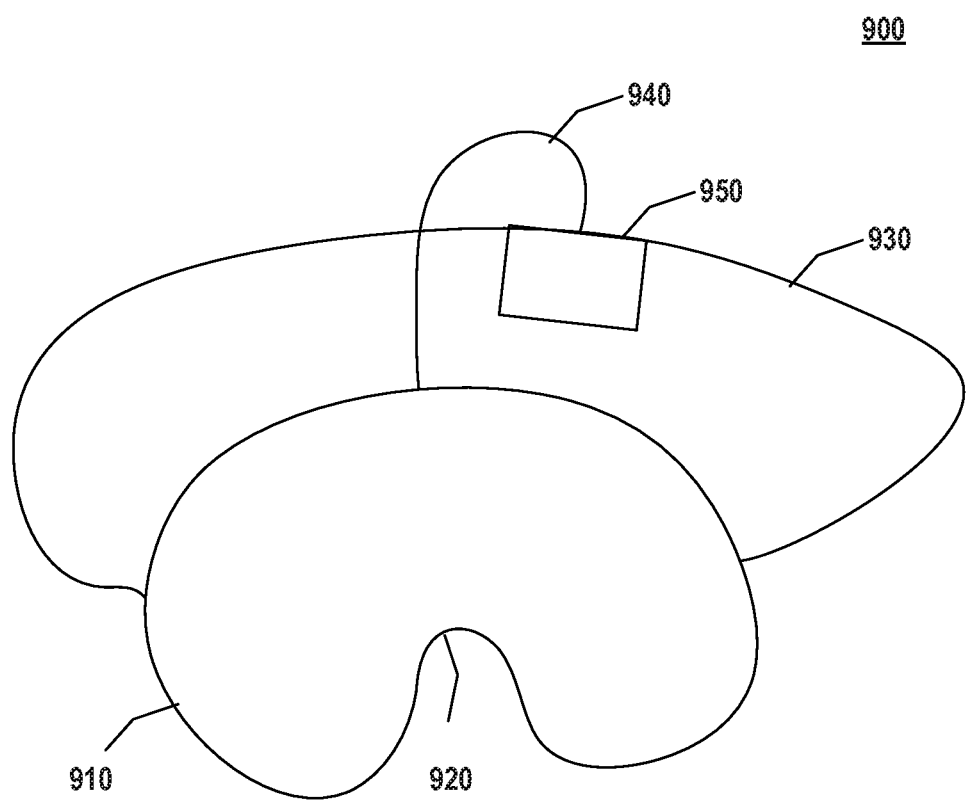
FIG. 9 illustrates further display glasses according to certain embodiments.

FIG. 9 illustrates a further embodiment of display glasses 900 according to certain embodiments of the present disclosure. As shown in FIG. 9, a mask 910 may be provided to cover both eyes of a wearer, with a saddle 920 to accommodate the wearer's nose. A latitudinal band 930 may be configured to secure the mask 910 to the wearer's face. A longitudinal band 940 may also be provided to help reduce the burden from the saddle 920 onto the wearer's nose, or for other purposes. The above-described sensors may be incorporated into the latitudinal band 930 or longitudinal band 940, or both. In certain embodiments, additional bands may be provided, or an entire cap or helmet may be provided. The mask 910 may be worn similar to ski goggles. The mask 910 may incorporate cameras to monitor the wearer's eyes, as described above. In certain embodiments, a counter-ballast 950 may be provided to help balance the weight of the display glass. Counter-ballast 950 may simply be a weight, but may optionally be a functional box, such as a battery pack, a transceiver section, or the like.

In certain embodiments, a constellation of electrodes or other sensors may be provided as a cap to be placed on the wearer's head. The sensors may be connected by a flexible or rigid net, by a sheet of fabric, or any other desired construction.

Figure 10:
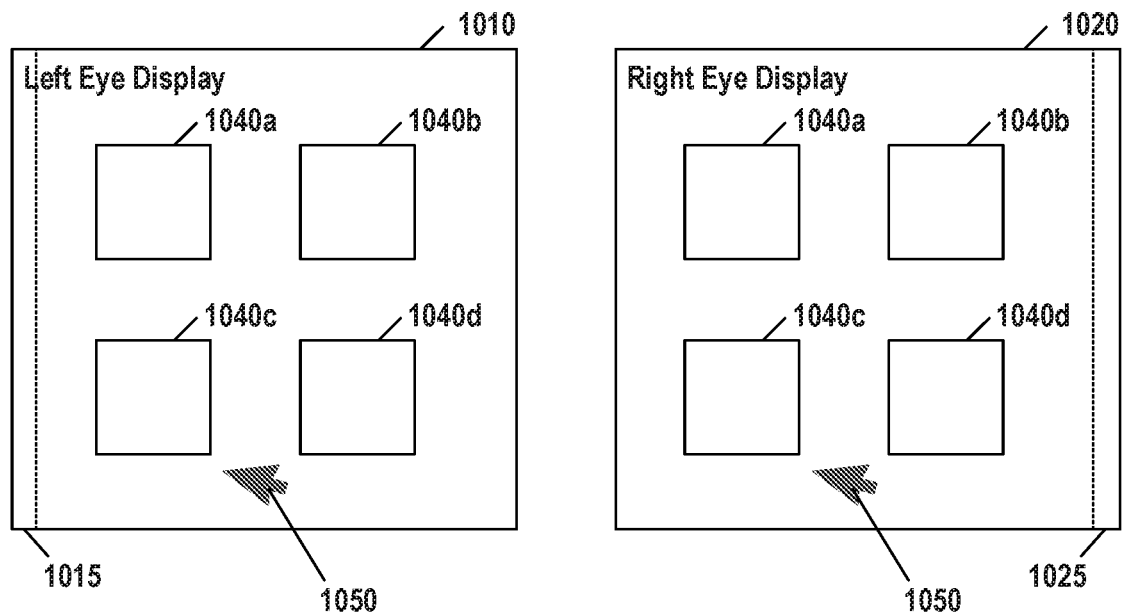
FIG. 10 illustrates a graphical user interface (GUI) according to certain embodiments.

FIG. 10 illustrates a graphical user interface (GUI) 1000 according to certain embodiments. As shown in FIG. 10, a GUI 1000 can include a left eye display 1010 and a right eye display 1020. In a monocular embodiment, only a single display may be used. In certain embodiments, a single panel of pixels may provide both the left eye display 1010 and right eye display 1020. Depending on the angle of view of the wearable glasses, the true left edge 1015 of the display may be viewable only on the left eye display 1010. On the other hand, the true right edge 1025 of the display may be viewable only on the right eye display 1020.

There may be four options 1040*a*, 1040*b*, 1040*c*, and 1040*d*, presented in the GUI 1000. Each of the four options 1040*a*, 1040*b*, 1040*c*, and 1040*d* may be shown on each of left eye display 1010 and right eye display 1020. A cursor 1050 may be shown, and the cursor may be controlled using the brain monitor subsystem described above, the muscle monitoring subsystem described above, eye tracking, or any other desired user interface. Optionally, the cursor 1050 may not be displayed, but the system may keep track of a focal point of the wearer without showing a cursor. This track of the focal point may be transparent to the wearer or may be provided to the wearer by, for example, highlighting one of the options when the wearer's focal point is on that option. For example, if the wearer looks at option 1040*c*, option 1040*c* may change color, blink, or may have a bezel added to its edge. Other highlighting methods are also permitted.

Various implementations of the above-described apparatuses and methods are possible. For example, a wearable apparatus for display glasses can include a display that includes a pair of screens configured to be mounted in front of respective eyes of a face of a wearer of the apparatus. The pair of screens may be variously implemented. For example, a projector in the display glasses may project an image onto an inner surface of the display glasses that may then be observed by the wearer of the display glasses. In another alternative, the display glasses may include two pixel areas positioned respectively in front of each eye of the wearer. The pixel areas may be implemented using a liquid crystal display (LCD), organic light emitting diode (OLED), light emitting diode (LED), or other display technology.

The display can be configured to provide a display of information to the wearer. For example, the display may present a display of information in a similar manner to the way in which information is displayed on the screen of a television, computer monitor, or the like. The information can include at least two options for selection. For example, the options can be presented as tiles, radio buttons, or positions on a wheel. Other ways of presenting the options are also permitted.

The wearable apparatus can include a brain monitor configured to track brain wave activity of the wearer. As explained above, an example of such a brain monitor is an EEG device.

The wearable apparatus can include a processor configured to identify one of the at least two options as selected based on the brain wave activity tracked by the brain monitor. The processor can be implemented as a general-purpose processor running software, as an application-specific integrated circuit (ASIC), or in any other desired way.

The wearable apparatus can further include an electroencephalogy electrode configured to detect an electric field within a brain of the wearer. The brain wave monitor can be configured to track the brain wave activity based on output of the electroencephalogy electrode. For example, the electroencephalogy electrode may provide a string of bits to the brain wave monitor, and the brain wave monitor may interpret these bits. The brain wave monitor may be a separate hardware processor from the processor of the display glasses. Alternatively, the brain wave monitor may be implemented on the same processor as the processor of the display glasses. The display glasses may also include further processors, such as graphics processing units (GPUs) for processing images to be displayed on the display glasses.

The electroencephalogy electrode can be mounted in at least one of a temple of the apparatus, a longitudinal band of the apparatus, or a latitudinal band of the apparatus. As mentioned above, in other implementations, a web of electroencephalogy electrodes can be provided to blanket the wearer's head.

The processor of the display glasses can include a neural network configured to identify the one of the at least two options based on training. This neural network may be a convolutional neural network, a deep convolutional network, or any other desired neural network.

The wearable apparatus can further include a camera configured to monitor eye position of the wearer. As discussed above, more than one camera may be used, and the camera can be any suitable visible light or infrared light sensing device. The processor can be configured to identify the one of the at least two options based on the brain wave activity in combination with the eye position. In certain embodiments, a separate hardware processor may be dedicated to eye tracking.

The processor can be configured to identify the selection of the one of the at least two options by correlating the eye position to a displayed position of one of the at least two options at a time when a mental determination is detected by the brain monitor. Thus, for example, the processor can keep track of eye position over time, and when the brain monitor determines that a selection is being made, the processor can pick the option based on the eye position. For example, if the wearer is presented with a panel on the left side of the screen and a panel on the right side of the screen, if the wearer is looking at the panel on the left side of the screen when brain waves representative of a decision to select are detected, the processor can select the option that was displayed at the left side of the screen. In certain embodiments, when there are many options displayed, the system may provide a multi-level selection process, where a patch of options representing a subset of the total options in a sight direction are selected, and that patch of options is then presented in a larger size in a next round. For example, 64 tiles may initially be presented. Based on a determination of the wearer's eye position, eight of the 64 tiles may be presented in a larger size in the next selection round. Similarly, if a rotating wheel is used in a first round, the options at the current wheel position as well as several positions before or after the current wheel position may be provided for selection in a second round.

The wearable apparatus can further include an electromyograph device configured to track the muscle activity of the wearer, as described above. The processor can be configured to identify the one of the at least two options based on the brain wave activity in combination with the muscle activity tracked by the electromyograph device. For example, the muscle activity may be used analogously to the way that eye tracking is used in the preceding examples.

The processor can be configured to identify the selection of the one of the at least two options by correlating the brain wave activity to a displayed content of one of the at least two options at a time when a predetermined muscular action is detected by the electromyograph.

The wearable apparatus can include a saddle or a pair of pads. The saddle or pair of pads can be configured to engage a nose of a wearer on the face of the wearer and to support the display in front of the face of the wearer. Other support structures may include bands, a crown structure, or a cap or a helmet structure. Other implementations are also possible.

The processor can be configured to identify the one of the at least two options based on a number of events detected by the brain monitor. For example, if a single brain activity is detected, this may correspond to a "yes," whereas if two brain activities of a given type are detected, this may correspond to a "no." The brain activity may be based on muscular control, such that an action of clenching or unclenching a jaw or first may be detected.

In another example, a wearable apparatus for display glasses can include a display that includes a pair of screens configured to be mounted in front of respective eyes of a face of a wearer of the apparatus. The display can be configured to provide a display of information to the wearer. The information can include at least two options for selection. The display may be variously implemented, as described above.

The wearable apparatus may also include an electromyograph device configured to track the muscle activity of the wearer. The wearable apparatus may further include a processor configured to identify one of the at least two options as selected based on the muscle activity tracked by the electromyograph device.

The wearable apparatus may further include a brain monitor configured to track brain wave activity of the wearer. The processor may be configured to identify the one of the at least two options based on the brain wave activity in combination with the muscle activity tracked by the electromyograph device, as described above.

The processor may be configured to identify the selection of the one of the at least two options by correlating the brain wave activity to a displayed content of one of the at least two options at a time when a predetermined muscular action is detected by the electromyograph.

The wearable apparatus may include an electroencephalogy electrode configured to detect an electric field within a brain of the wearer. The brain wave monitor can be configured to track the brain wave activity based on the output of the electroencephalogy electrode.

The wearable apparatus may further include an electromyograph electrode configured to detect muscle activity of the wearer. The electromyograph device may be configured to track the muscle activity based on the output of the electromyograph electrode. In certain embodiments, the same electrode may be configured to operate as both an electromyograph electrode and an electroencephalogy electrode. In other embodiments, different electrodes may be used.

The electromyograph electrode may be mounted in at least one of a temple of the apparatus, a longitudinal band of the apparatus, or a latitudinal band of the apparatus. Other positions are also possible, as described above.

The processor can include a neural network configured to identify the one of the at least two options based on training. As mentioned above, various neural networks can be used. These neural networks may include a recurrent neural network, a long/short term memory, and a gated recurrent unit. Other neural networks and combinations thereof are also permitted.

The wearable apparatus can include a camera configured to monitor the eye position of the wearer. The processor can be configured to identify the one of the at least two options based on the muscle activity in combination with the eye position.

For example, the processor can be configured to identify the selection of the one of the at least two options by correlating the eye position to a displayed position of one of the at least two options at a time when muscle activity is detected by the electromyograph device.

The processor can be configured to identify the one of the at least two options based on a number of events detected by the electromyograph device. For example, if one muscle movement is detected, a first option may be picked, whereas if two muscle movements of the same kind or of different kinds are detected, a second option may be picked, and so on. In a further embodiment, the muscle movements may be translated into a determination of a hand position of the wearer, and the option may be picked based on mapping the hand position to a displayed option position.

The above detailed description of the disclosure and the examples described therein have been presented for the purposes of illustration and description only and not by limitation. It is therefore contemplated that the present disclosure covers any and all modifications, variations or equivalents that fall within the spirit and scope of the basic underlying principles disclosed above and claimed herein.

What is claimed is:

1. A wearable apparatus for display glasses, comprising: a display comprising a pair of screens configured to be mounted in front of respective eyes of a face of a wearer of the apparatus and configured to provide a display of information to the wearer, the information comprising at least two options for selection; a brain monitor configured to track brain wave activity of the wearer and to detect a mental determination; and a processor configured to identify one of the at least two options as selected based on the brain wave activity tracked by the brain monitor and the mental determination detected: an electromyograph device configured to track least two options based on the brain wave activity in combination with the muscle activity tracked by the electromyograph device.

2. The wearable apparatus of claim 1, further comprising:
    an electroencephalogy electrode configured to detect an electric field within a brain of the wearer, wherein the brain wave monitor is configured to track the brain wave activity based on output of the electroencephalogy electrode.

3. The wearable apparatus of claim 2, wherein the electroencephalogy electrode is mounted in at least one of a temple of the apparatus, a longitudinal band of the apparatus, or a latitudinal band of the apparatus.

4. The wearable apparatus of claim 1, wherein the processor comprises a neural network configured to identify the one of the at least two options based on training.

5. The wearable apparatus of claim 1, further comprising:
a camera configured to monitor eye position of the wearer, wherein the processor is configured to identify the one of the at least two options based on the brain wave activity in combination with the eye position.

6. The wearable apparatus of claim 5 wherein the processor is configured to identify selection of the one of the at least two options by correlating the eye position to a displayed position of one of the at least two options at a time when the mental determination is detected by the brain monitor.

7. The wearable apparatus of claim 1, wherein the processor is configured to identify selection of the one of the at least two options by correlating the brain wave activity to a displayed content of one of the at least two options at a time when a predetermined muscular action is detected by the electromyograph device.

8. The wearable apparatus of claim 1, further comprising:
a saddle or a pair of pads, wherein the saddle or pair of pads is configured to engage a nose of a wearer on the face of the wearer and to support the display in front of the face of the wearer.

9. The wearable apparatus of claim 1, wherein the processor is configured to identify the one of the at least two options based on a number of events detected by the brain monitor.

10. A wearable apparatus for display glasses, comprising:
a display comprising a pair of screens configured to be mounted in front of respective eyes of a face of a wearer of the apparatus and configured to provide a display of information to the wearer, the information comprising at least two options for selection;
an electromyograph device configured to track muscle activity of the wearer;
a processor configured to identify one of the at least two options as selected based on the muscle activity tracked by the electromyograph device; and
a brain monitor configured to track brain wave activity of the wearer, and
wherein the processor is configured to identify the one of the at least two options based on the brain wave activity in combination with the muscle activity tracked by the electromyograph device.

11. The wearable apparatus of claim 10, wherein the processor is configured to identify selection of the one of the at least two options by correlating the brain wave activity to a displayed content of one of the at least two options at a time when a predetermined muscular action is detected by the electromyograph device.

12. The wearable apparatus of claim 10, further comprising:
an electroencephalogy electrode configured to detect an electric field within a brain of the wearer, wherein the brain wave monitor is configured to track the brain wave activity based on output of the electroencephalogy electrode.

13. The wearable apparatus of claim 10, further comprising:
an electromyograph electrode configured to detect muscle activity of the wearer, wherein the electromyograph device is configured to track the muscle activity based on output of the electromyograph electrode.

14. The wearable apparatus of claim 13, wherein the electromyograph electrode is mounted in at least one of a temple of the apparatus, a longitudinal band of the apparatus, or a latitudinal band of the apparatus.

15. The wearable apparatus of claim 10, wherein the processor comprises a neural network configured to identify the one of the at least two options based on training.

16. The wearable apparatus of claim 10, further comprising:
a camera configured to monitor eye position of the wearer, wherein the processor is configured to identify the one of the at least two options based on the muscle activity in combination with the eye position.

17. The wearable apparatus of claim 16, wherein the processor is configured to identify selection of the one of the at least two options by correlating the eye position to a displayed position of one of the at least two options at a time when muscle activity is detected by the electromyograph device.

18. The wearable apparatus of claim 10, wherein the processor is configured to identify the one of the at least two options based on a number of events detected by the electromyograph device.

19. The wearable apparatus of claim 10, wherein the electromyograph device is configured to track jaw muscle activation, jaw muscle deactivation, or both jaw muscle deactivation and jaw muscle activation.

20. The wearable apparatus of claim 19, wherein the processor is configured to identify the one of the at least two options based on a number of jaw muscle activations, jaw muscle deactivations, or jaw muscle activations and jaw muscle deactivations detected within a predetermined time period.

21. A wearable apparatus for display glasses, comprising:
a display comprising a pair of screens configured to be mounted in front of respective eyes of a face of a wearer of the apparatus and configured to provide a display of information to the wearer, the information comprising at least two options for selection;
an electromyograph device configured to track muscle activity of the wearer;
a brain monitor configured to track brain wave activity of the wearer and to detect a mental determination; and
a processor configured to identify one of the at least two options as selected based the brain wave activity detected by the brain monitor in combination with the muscle activity tracked by the electromyograph device.

* * * * *